(12) United States Patent
Milhofer et al.

(10) Patent No.: US 6,294,686 B1
(45) Date of Patent: Sep. 25, 2001

(54) ASPARTAME CRYSTALS AND PROCESS FOR THE PREPARATION THEREOF

(75) Inventors: Helga F. Milhofer; Nissim Garti; Alexey Kamishny, all of Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 09/530,355

(22) PCT Filed: Oct. 29, 1998

(86) PCT No.: PCT/IL98/00524

§ 371 Date: Jun. 28, 2000

§ 102(e) Date: Jun. 28, 2000

(87) PCT Pub. No.: WO99/21876

PCT Pub. Date: May 6, 1999

(30) Foreign Application Priority Data

Oct. 29, 1997 (IL) .......................................... 122068

(51) Int. Cl.[7] .................................................. C07C 229/00
(52) U.S. Cl. .................................................. 560/41; 560/40
(58) Field of Search .......................................... 560/40, 41

(56) References Cited

FOREIGN PATENT DOCUMENTS

| 0 119 837 |   | 9/1984 | (EP) . |
|---|---|---|---|
| 0680971 | * | 11/1995 | (EP) . |
| 0 718 306 |   | 6/1996 | (EP) . |
| 0751146 | * | 1/1997 | (EP) . |

OTHER PUBLICATIONS

Kirk–Othmer Encyclopedia of Chemical Technology, vol. 9 (1995), 4th edition, pp. 393–412.*
Kirk–Othmer Encyclopedia of Chemical Technology vol. 11 (1995), 4th edition, pp. 813–814.*

* cited by examiner

Primary Examiner—Paul J. Killos
Assistant Examiner—Mahreen Chaudhry
(74) Attorney, Agent, or Firm—Foley & Lardner

(57) ABSTRACT

The invention provides a method of preparing new crystal forms of aspartame utilizing microemulsions comprising: (a) introducing aspartame into a microemulsion formed from an oil phase, an aqueous phase and at least one emulsifier, (b) destabilizing the microemulsion to effect recrystallization of aspartame; (c) separating solid phase crystals from the liquid phase in which they are contained; and (d) cleaning the crystals to remove traces of the oil phase and surfactant.

21 Claims, 17 Drawing Sheets

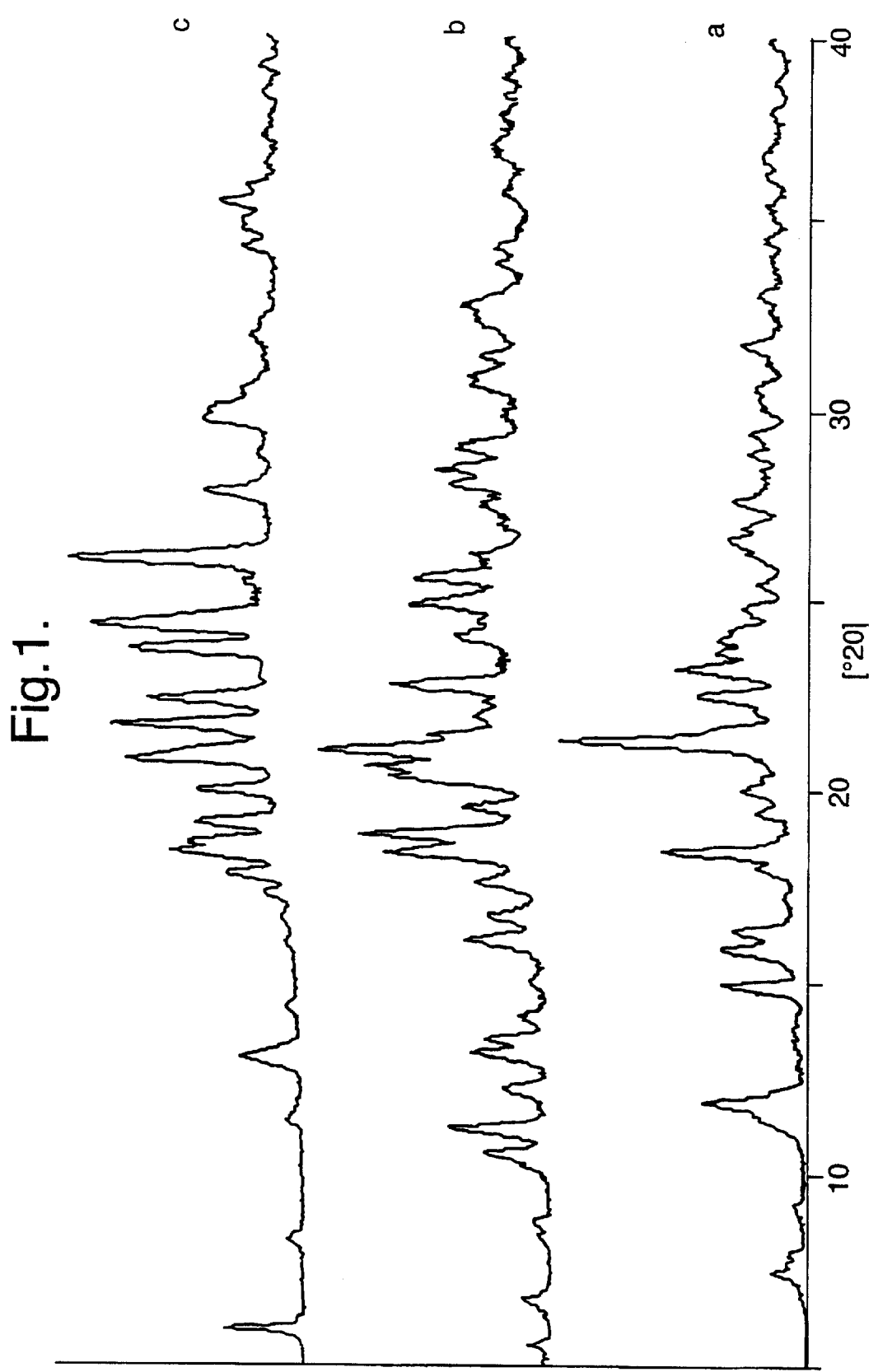

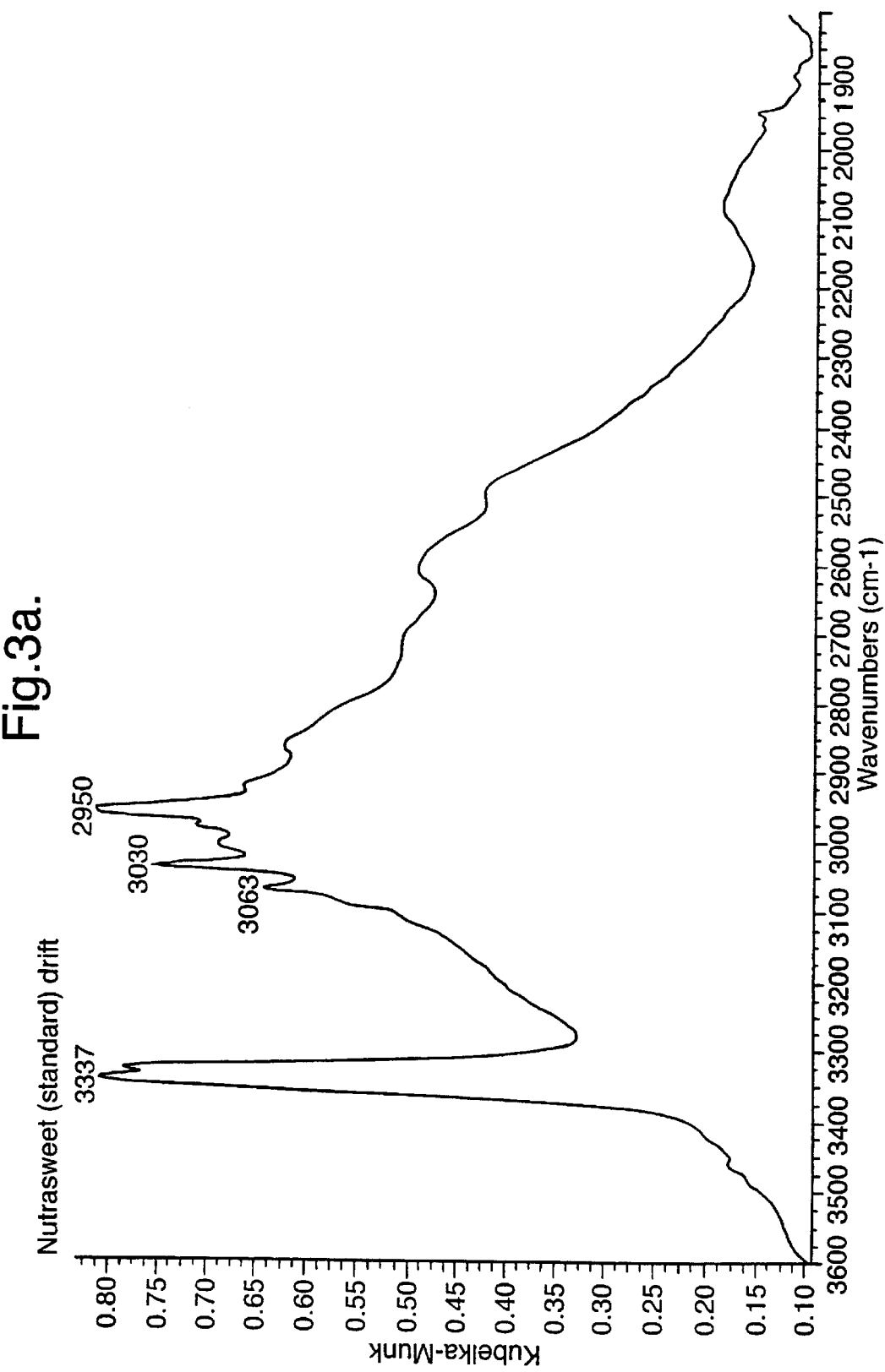

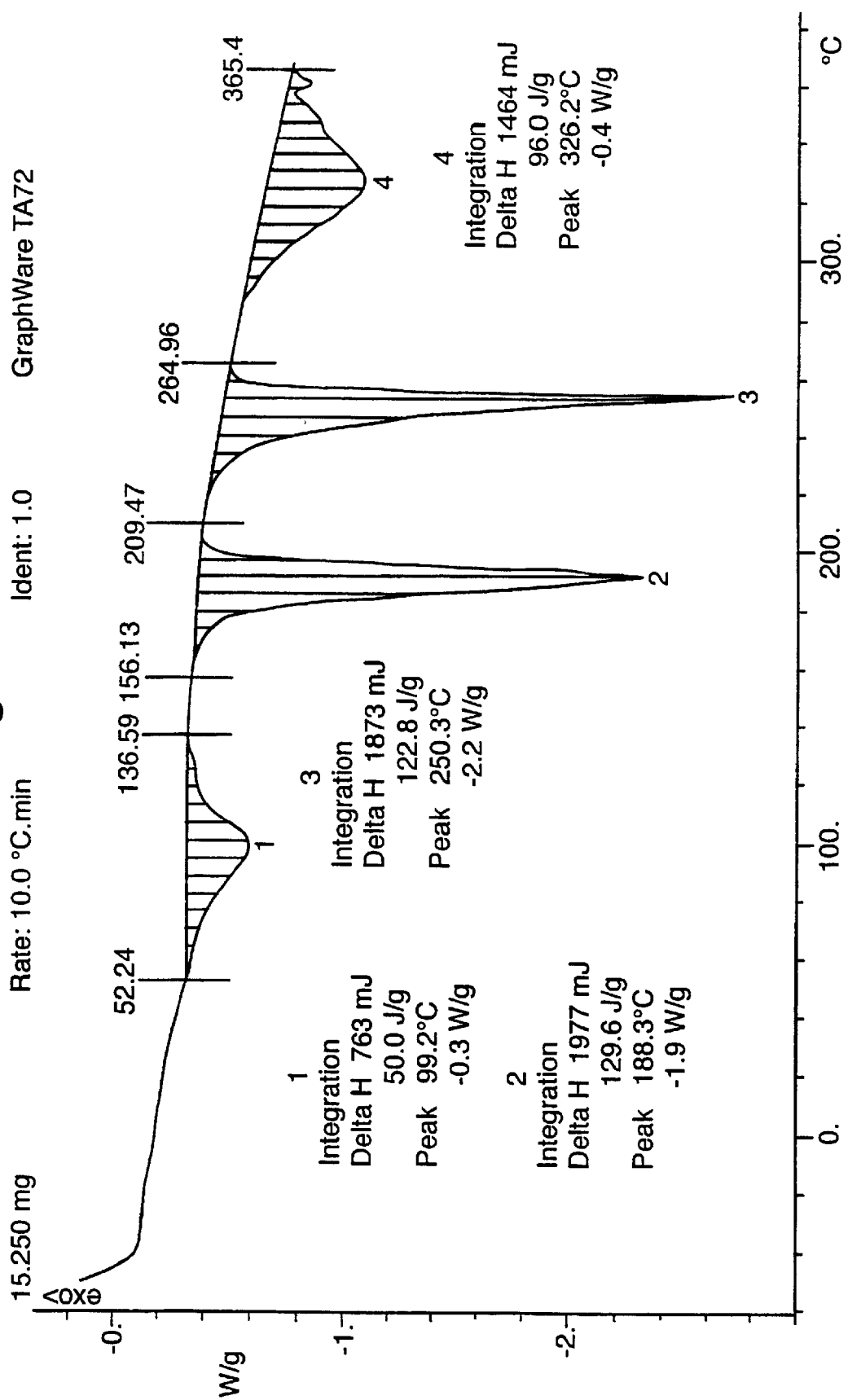

ASPARTAME CRYSTALS AND PROCESS FOR THE PREPARATION THEREOF

TECHNICAL FIELD

The present invention relates to aspartame. More particularly the present invention relates to a novel method for the preparation of aspartame and a new crystal form of aspartame obtained by this method.

BACKGROUND ART

Aspartame (N-L-a-aspartyl-L-phenylalanine methyl ester) hereinafter referred to as APM, was first described and claimed in U.S. Pat. No. 3,492,131 issued in 1970 by Searle. Since then, it dominates the market of low calorie artificial sweeteners, which are being increasingly used in both low calorie and "normal" food products.

The APM molecule is a dipeptide composed of a highly hydrophilic aspartyl residue and a hydrophobic (phenylaianine methyl ester) entity and is zwitterionic at the aspartyl end. To date four polymorphic forms (IA, IB, IIA and IIB) of APM have been described (European Patent Application 0119837 B1, issued to Ajinomoto in 1988).

Compared to other artificial sweeteners APM has several advantages:

a) high sweetening power (300–400 that of sucrose as compared to 300 for saccharin and 30 for cyclamate);

b) no after taste; and c) relatively good compatibility to human consumption (the acceptable daily intake in mg/kg/day of APM is 0–40 as compared to cyclamate 0–11, acesulfame 0–9 and saccharin 0–2.5).

DISCLOSURE OF THE INVENTION

In the present invention microemulsions are utilized to prepare new crystal forms of aspartame. Microemulsions are homogeneous, thermo-dynamically stable systems, consisting of submicron-size droplets of water dispersed within an immiscible organic (oil) phase or vice versa, oil droplets dispersed within a continuous aqueous phase. The droplets are protected against coalescence by adsorbed layers of suitable surfactants or a surfactant and cosurfactant, (usually an alcohol), and thus stabilized. Microemulsions can be destabilized by changing the specific conditions under which they are formed (i.e. by changing the temperature, pressure and/or by addition of excess of water or a suitable reagent such as a salt, base, etc).

The term "microemulsion", as used herein, is intended to denote standard microemulsions, as well as any self-assembly of surfactants capable of solubilizing another liquid phase, i.e., micelles, mixed micelles, liposomes, neosomes, lyotropic liquid crystals, etc.

According to the present invention there is provided a novel method for the crystallization - recrystallization of aspartame. More specifically, the present invention provides a method of preparing new crystal forms of aspartame utilizing microemulsions comprising introducing aspartame into a microemulsion formed from an oil phase, an aqueous phase and at least one emulsifier; destabilizing said microemulsion to effect recrystallization of aspartame; separating solid phase crystals from the liquid phase in which they are contained; and cleaning said crystals to remove traces of the oil phase and surfactant.

This approach provides new possibilities to modify crystallization, thus bringing about new crystal forms.

In preferred embodiments of the present invention said microemulsion is formed from an oil phase, an aqueous phase and an emulsifier. Aspartame is introduced into the microemulsion or into the aqueous phase prior to preparing the microemulsion.

In a first preferred embodiment of the present invention said microemulsion is a water-in-oil microemulsion, stabilized by a zwitterionic, cationic, food-grade nonionic or anionic emulsifier. In preferred embodiments said microemulsion is stabilized by a double-chained anionic emulsifier or by a food-granule nonionic emulsifier. Preferred emulsifiers in this embodiment are sodium diisooctyl sulfosuccinate (AOT) and/or a food-grade surfactant consisting of 10% wt/wt L-α-phosphatydilcholine and 90% wt/wt of monoglycero-oleate dissolved in propyleneglycol (ATMOS 300 from ICI Co).

It is to be noted that said emulsifiers can be used alone, or said microemulsion can be achieved by utilizing mixtures or blends of emulsifiers, including any type of cosolvent or coemulsifier, wherein in the literature alcohol is sometimes referred as a cosolvent and sometimes as a coemulsifier.

Preferably in said embodiments said oil is selected from the group consisting of hydrocarbons, liquid triglycerides, alcohols, acids, ketones, food-grade esters, aldehydes, terpenes, essential oils and oleoresins.

Thus, e.g., based on the above principles, there are now prepared according to the present invention, two new crystal forms, form III and form IV of aspartame. Form III was obtained by solubilization of commercial aspartame in water/isooctane microemulsions stabilized by diisooctyl sulfosuccinate (AOT) and its crystallization by subsequent cooling of the microemulsion. Commercial aspartame obtained by courtesy of NUTRASWEET Co, Switzerland (hereinafter NUTRASWEET® aspartame) was used for all experiments and as a standard for comparison with the new products.

Form III of aspartame, hereinafter referred to as APM III, is characterized by:

(a) an X-ray diffraction powder pattern (angles of diffraction) as set forth in FIG. 1b herein;

(b) an FTIR spectrum as represented in FIGS. 3b and 4b herein;

(c) TG/DTA and DSC patterns as represented in FIG. 5 appended hereto;

(d) The NMR spectrum of the dissolved product is identical to the NHR spectrum of NUTRASWEET® as per FIG. 8a; and (e) improved dissolution kinetics as compared to commercial NUTRASWEET® aspartame as shown in FIG. 9 herein.

When kept in a closed vial APM III was stable for at least one year.

Different crystal forms of aspartame can also be obtained by crystallizing commercial aspartame from edible microemulsions, such as water/oil/lecithin/mono and diglycerol oleate and others. Thus another new crystal form, form IV aspartame, hereinafter referred to as APM IV, was obtained from w/o microemulsions comprising soybean oil as the oil phase, stabilized by the food-grade surfactant ATMOS 300. APM IV is an adduct of aspartame with propylene glycol with a 1:1 molar ratio. The product is characterized by:

(a) an X-diffraction powder pattern (FIG. 1c) which is distinctly different from the patterns of forms IA, IB, IIA, IIB as described in European patent No. 0119837B1 and from the pattern of APM III (FIG. 1b).

(b) an FTIR spectrum as shown in FIGS. 3c and 4c (c) Thermogravimetric (TG and DTA) and differential scanning calorimetric patterns (FIG. 6) and (d) the H-NMR spectrum of the product dissolved in D2O (FIG. 8b).

While the invention will now be described in connection with certain preferred embodiments in the following examples and with reference to the appended figures so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

DESCRIPTION OF PREFERRED EMBODIMENTS

EXAMPLE 1

22 g of aspartame were solubilized by mechanical stirring in a microemulsion containing 234 g (65%) of isooctane, 36 g (10%) of water and 90 g (25%) AOT at 65° C. The microemulsion was then cooled at a rate of 1° C. per min. with constant stirring to a final temperature of 5° C. and stirred at this temperature for an additional two hours to induce crystallization. After the onset of crystallization stirring was discontinued and the suspension stored overnight at 4° C. to complete crystallization. A gel-like product was obtained which was filtered and then repeatedly washed with hexane until the product appeared crystalline. Every washing cycle consisted of stirring the product in the presence of hexane and subsequent filtration. To remove hexane, the final product was kept for 48 h in a vacuum oven at 40° C. The crystals gave an X-ray powder pattern characteristic of form III aspartame.

EXAMPLE 2

20 g of NUTRASWEET® aspartame were dissolved by mechanical stirring in a microemulsion containing 262.5 g (70%) isooctane, 37.5 g (10%) water and 75 g (20%) AOT at 56° C. The microemulsion was then cooled at a rate of 1° C./3 min to a final temperature of 5° C. under constant mechanical stirring. Under these conditions crystallization commenced at approx. 20–30° C. To complete crystallization, the suspension was stored overnight at 4° C. A gel-like product was obtained which was filtered and then repeatedly washed with hexane until the content of AOT decreased to<0.25% wt/wt. The product was then kept in a vacuum oven for 2 hours at 70° C. X-ray spectroscopy confirmed that the product was form III aspartame.

EXAMPLE 3

The crystallization procedure was as described in example 2. After crystallization was completed the gel-like suspension was diluted with 250 ml of hexane and stirred approx. 1 hour. The filtering process was thereby greatly improved. After filtration washing with hexane was continued until the content of AOT was not greater than 0.25% wt/wt. The product was dried for 2 hours at 70° C. and the presence of form III aspartame confirmed by X-ray spectroscopy.

EXAMPLE 4

7.00 g of aspartame were mechanically stirred into a hot (65° C.) microemulsion containing 212.5 g (42.5%) of soybean oil, 37.5 g (7.5%) of water and 250.0 g (50%) of surfactant. The surfactant consisted of 90% ATMOS 300 and 10% phosphatidylcholine (PC, 40% pure from SIGMA). The resulting suspension was filtered and the clear microemulsion was slowly cooled to 4° C. Crystallization of aspartame commenced after several hours. To complete crystallization the suspension was kept for three days at 4° C. in a cold room or thermostat. Before filtration, 200 ml of hexane were added to the resulting product and the suspension was stirred at 4° C. for one hour. The crystals of aspartame obtained after the first filtration were repeatedly cleaned with hexane at 4° C. until the product contained approximately 20% wt/wt of propyleneglycol which amounts to a 1:1 molar ratio of aspartame and propyleneglycol. To remove hexane the final product was heated for 2 hours at 55° C. The crystals exhibited an XRD powder pattern as shown in FIG. 1c and an H-NMR spectrum as shown in FIG. 8b.

EXAMPLE 5

0.60 g of aspartame were mechanically stirred into a hot (65° C.) microemulsion containing 29.75 g (42.5%) of soybean oil, 5.25 g (7.5%) of water and 35 g (50%) of surfactant. The surfactant consisted of 90% ATMOS 300 and 10% phosphatidylcholine (PC, 99% pure from LIPOID GmbH). The resulting suspension was filtered and the clear microemulsion was slowly cooled to 4° C. Crystallization of aspartame commenced after several hours. To complete crystallization the suspension was kept for three days at 4° C. in a cold room or thermostat. Before filtration, 100 ml of hexane were added to the resulting product and the suspension was stirred at 4° C. for one hour. The crystals of aspartame obtained after the first filtration were repeatedly cleaned with hexane at 4° C. until the product contained approx 20% wt/wt of propyleneglycol which amounts to a 1:1 molar ratio of aspartame and propyleneglycol. To remove hexane the final product was heated for 2 hours at 55° C. The crystals exhibited an XRD powder pattern an H-NMR spectrum of APMIV.

BRIEF DESCRIPTION OF THE DRAWINGS

Referring now to the figures in detail:

FIG. 1 shows X-ray powder patterns of (a) NUTRASWEET® aspartame, (b) form III aspartame, (c) form IV aspartame. NUTRASWEET® aspartame has the characteristics of type IB aspartame as described in European patent No. 0119837B1.

FIG. 6 shows results of thermal analysis of form IV aspartame.

FIG. 7 shows results of thermal analysis of NUTRASWEET® aspartame. FIG. 7a illustrates DSC and FIG. 7b illustrates TG and DTA spectra.

FIG. 8 is an HNMR spectra of aspartame dissolved in 99,9% D$_2$O. FIG. 8a illustrates NUTRASWEET® aspartame and FIG. 8b illustrates form IV aspartame. The spectrum of form III is identical to FIG. 9a.

FIG. 9 shows the dissolution kinetics of aspartame.

SOLUBILIZATION AND RECRYSTALLIZATION PROCEDURES

The amount of aspartame that could be solubilized in thermodynamically stable water/isooctane/AOT microemulsions depended on the amount of AOT in the microemulsions. At an aspartame/AOT molar ratio between 4 and 5 stable microemulsions, containing up to 30 gr/l of aspartame (i.e. about three times as much as in the same volume of water) were formed at room temperature. About 70% more aspartame (up to 50 gr/l) could be solubilized by heating the microemulsions up to 60° C. and stirring mechanically or sonicating. Such microemulsions were metastable but could be stored at room temperature without disturbance for at least one week - disturbance induced crystallization with concurrent breaking of the microemulsion.

About 7 times less aspartame could be solubilized in microemulsions containing water, soybean oil, phosphatydilcholine and Atmos 300 (see examples 4 and 5). The procedures following solubilization were the same for both types of microemulsions.

Microemulsions containing solubilized aspartame were destabilized by cooling thus inducing crystallization of forms III and IV of aspartame respectively. After completed crystallization the product consisted of a mixture of the respective form of aspartame with the emulsifier and some of the oil phase. The product was filtered and cleaned by repeated washing with hexane. At the end excess hexane was removed by drying in a vacuum oven at temperatures up to 75° C. Cleaning of form IV aspartame was terminated when the molar ration aspartame/propyleneglycol reached 1:1, which was ascertained by H-NMR spectroscopy. If the product was heated for 24 hours at 100° C. it converted to form IIA aspartame, which is described in European patent No. 0119837B1. For characterization, the dried products were compared with commercial aspartame provided by NUTRASWEET Co., Switzerland.

Characterization of the New Crystal Forms of Aspartame

Forms III and IV of aspartame are characterized by distinct X-ray powder diffraction patterns as well as changes in FTIR, TGA/DTA and DSC spectra, and HNMR spectra of the products dissolved in D$_2$O.

Figure 2A:
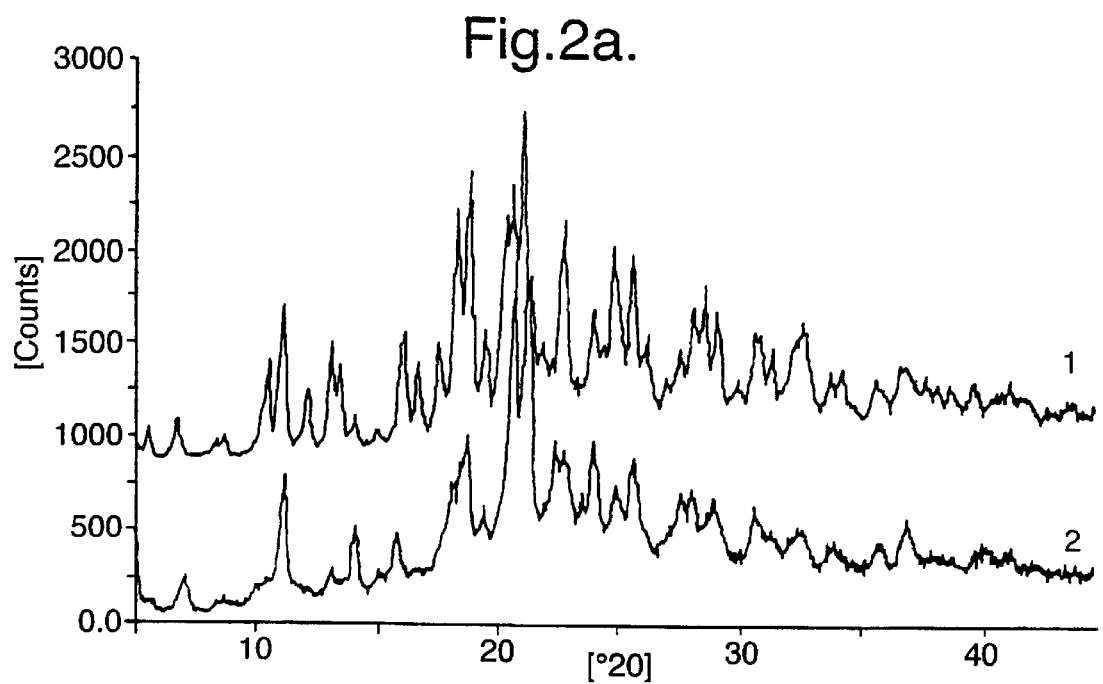
FIG. 2 represents X-ray powder patterns of: (a) form III (curve 1) compared to type IIA (curve2) aspartame; (b) form III (curve 1) compared to type IIB (curve 2) aspartame. Type IIA and IIB aspartame have been synthesized after European patent No. 0119837B1.
Figure 2B:
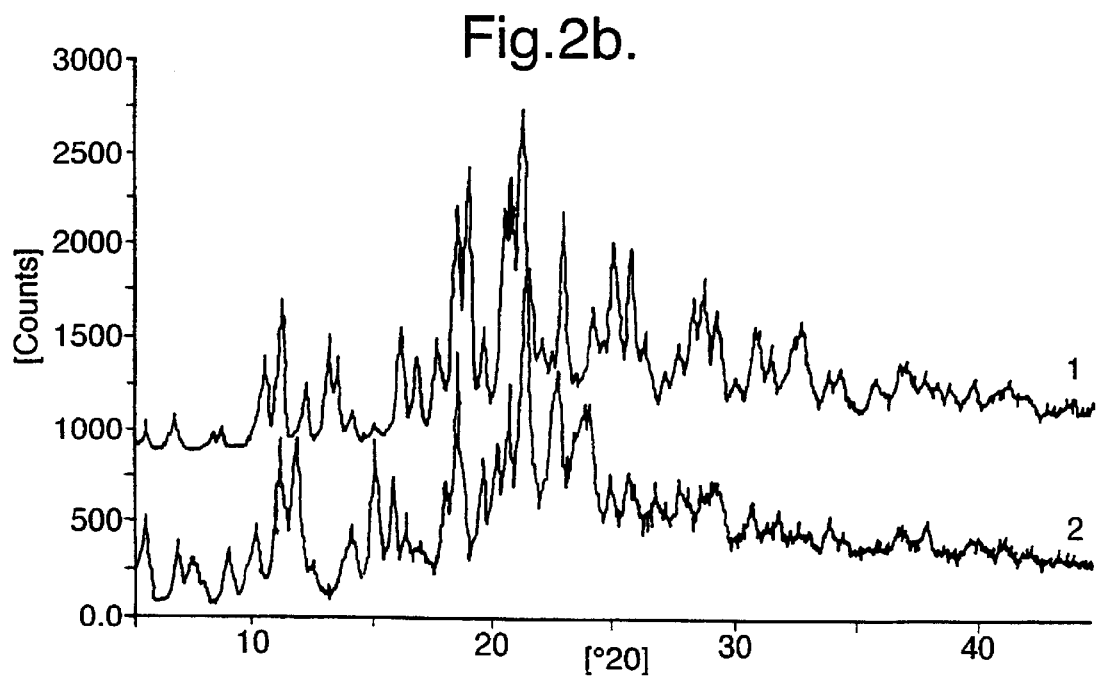

X-ray diffraction powder patterns (as shown in FIGS. 1, 2) were recorded under ambient conditions at angles of diffraction 2 θ between 5° and 40° on a Philips diffractometer (goniometer PW 1820) with CuKα radiation. Form III exhibits strong reflections (I>40%) at angles of diffraction 2 θ=5.64°, 6.81°, 10.56°, 11.25°, 12.25°, 13.18°, 13.59°, 21.09° and 25.71°, as well as a triplet at 18.37°, 18.52° and 18.90° and a doublet at 20.41° and 20.66°. Form IV exhibits strong reflections (Y>35%) at 2θ=6.00°, 13.04°, 19.14°, 19.92°, 20.78°, 21.71°, 22.40°, 23.81°, 24.25°, 26.11°, including a doublet at 18.33° and 18.70°. The differences between the respective diffraction patterns and those of previously known forms of aspartame are apparent from FIGS. 1 and 2. In FIG. 1 the diffraction patterns of forms III and IV spartame (FIGS. 1b and 1c) are compared to the pattern of NUTRASWEET® aspartame (FIG. 1a) which resembles type IB crystals shown in European patent No. 0119837B1.

In FIGS. 2a,b the diffraction pattern of form III is compared to patterns of forms IIA and IIB, synthesized by the present inventors after European patent No. 0119837B1. Also significant are differences between the spectra of form III, form IV and form IA (not compared here but represented in European patent No. 0119837B1). Thus it can be said that forms III and IV aspartame exhibit X-ray diffraction powder patterns which are distinctly different from those of forms IA, IB, IIA and IIB described in European patent No. 0119837B1, in addition to being distinct from each other.

FTIR spectra (taken by the drift method on a Nicolet 5 PC FTIR spectrometer, courtesy of TEVA laboratories, Jerusalem) show shifts towards lower wavenumbers of the N-H stretch frequency belonging to the amide group of the peptide bond in aspartame. The respective numbers are (in cm$^{-1}$): 3337 for NUTRASWEET, 3333 for form IV and 3307 for form III. Smaller, but recognizable shifts are apparent also in the range of the carbonyl stretching frequency of the peptide bond, i.e. the frequency (in cm$^{-1}$) 1669 for NUTRASWEET aspartame is shifted to 1660 for form III and to 1658 for form IV of aspartame. In addition the spectrum of form IV exhibits several peaks (marked with asterix) which are not present in the spectra of the control and can be assigned to propylene glycol (all assignments after C. N. R. Rao, Chemical Applications of Infrared Spectroscopy, Acad. Press New York, London 1963).

Figure 5A:
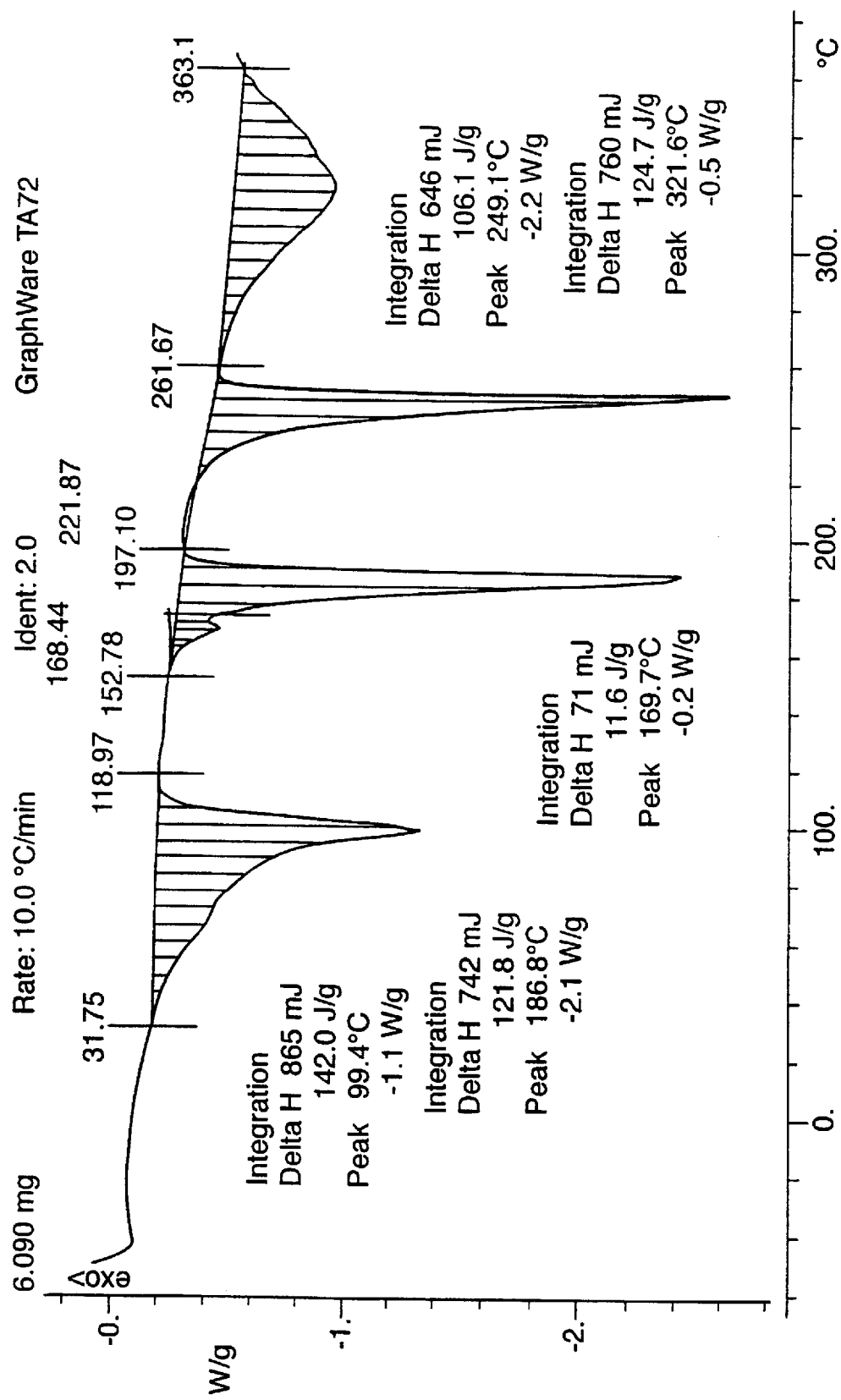
FIG. 5 shows results of thermal analysis of form III aspartame: (a) differential scanning calorimetry (DSC) and (b) corresponding TG and DTA spectra.

Thermal gravimetric and differential thermal analysis (TG/DTA); differential scanning calorimetry (DSC). Data were recorded on a Mettler 3000 system. For DSC measurements the capsules containing the powder were closed except for a small hole in the middle In FIGS. 5–7 DSC and the corresponding TG/DTA spectra characterizing form III (FIG. 5), form IV (FIG. 6) and NUTRASWEET aspartame (FIG. 7) are compared. The results obtained from form III and NUTRASWEET aspartame are in general agreement with each other and with literature data (A. Chauvet, H. De Saint-Julien, G. D. Maury and J. Masse, Thermochimica Acta 71 (1981) 79–91). The TG and DTA spectra exhibit dehydration peaks at 91° C. (61.5° C.–107.5° C., total weight loss -7% wt/wt) for form III, and at 109° (32.5° C.–135° C., total weight loss—3.7% wt/wt) for NUTRASWEET aspartame respectively. It appears that form III aspartame contains more hydration water.

Two decomposition peaks appear at 177.5° C. (-10.9 w %) and 324.5° C. for form III, and at 183.0° (-11.5% wt/wt) and 328.0° for NUTRASWEET aspartame, which compares well to decomposition peak I at 170° C.–200° C. (12.2 w %) and peak II at 250°–450° C. reported by Chauvet et al. According to these authors the first peak corresponds to the conversion of aspartame into diketopiperazine, while the second peak corresponds to the decomposition of the latter compound. Decomposition into diketopiperazine is apparent also by thermal microscopy, the point appearing in form III and NUTRASWEET aspartame at 197° C., while Chauvet et al. reported it between 180° and 185° C.

The corresponding DSC spectra exhibit four endothermal peaks, one of them due to dehydration and three in the range of melting and decomposition. The dehydration peak of form III aspartame (31.75–119° C., FIG. 5a) indicates that part of the water is loosely bound, but at least part of it is tightly bound crystal water, emerging near the boiling point. It should be noted that even when DSC spectra were taken from −100° C. at a rate of 5° C./min, no peak corresponding to free freezing water was detected.

The decomposition peaks recorded by DSC for form III aspartame are in accordance with those of NUTRASWEET aspartame and literature data (A. Chauvet, H. De Saint-Julien, G. D. Maury and J. Masse, Thermochimica Acta 71 (1981) 79–91) and have been reported to correspond to the decomposition of aspartame into diketopiperazine (187° C.–188° C.), fusion (249° C.–250° C.) and decomposition of the latter (322° C.–326° C.).

Figure 8A:
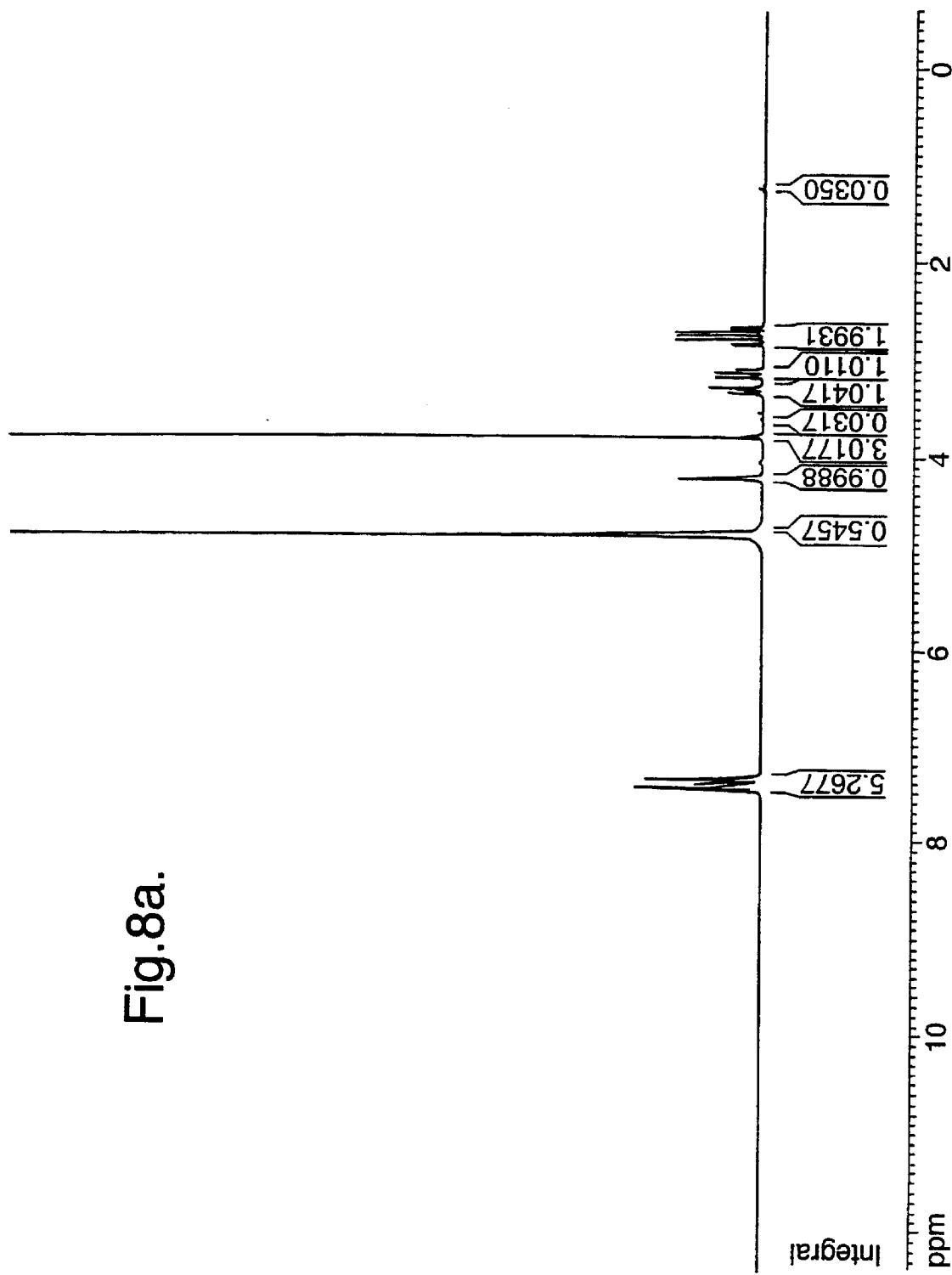
Figure 8B:
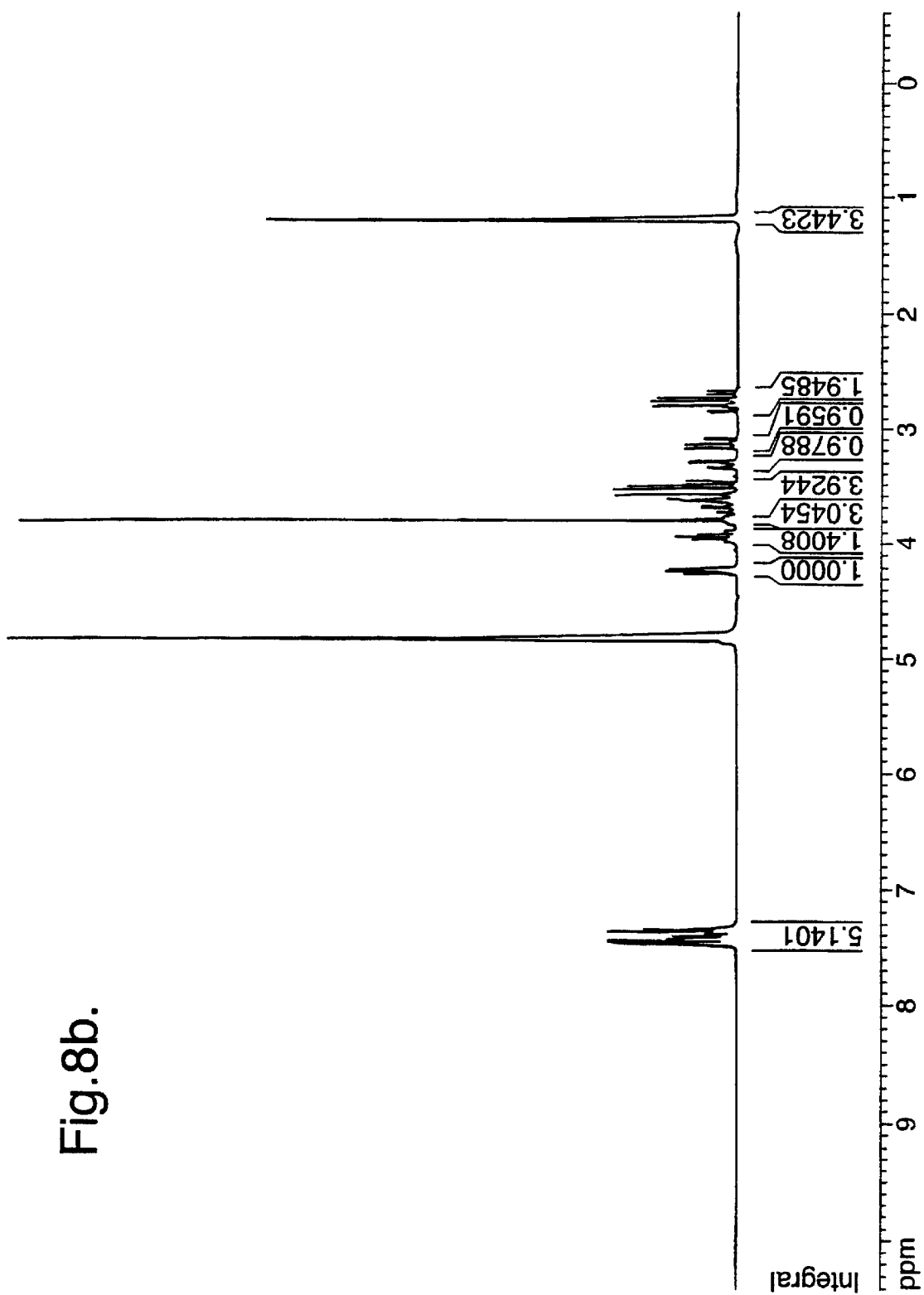

The differences observed in the TG/DTA and DSC spectra of form IV aspartame are more significant. The peak in the region corresponding to dehydration appears at 89° C. and the total weight loss is much larger than in form III and NUTRASWEET aspartame, i.e. −18.6% wt/wt. The following decomposition peaks appear at 157° C. (−17.3% wt/wt) and 335° C. In the DSC spectrum both the "dehydration peak" and the first decomposition peak are doublets, the latter being shifted towards lower temperature (i.e. 143° C. and 150.9° C. respectively). These differences can be explained by the presence of propylene glycol (PG) which is used as a solvent in ATMOS 300. The presence of PG is also apparent from the respective FTIR spectra (FIGS. 3b and 4b) and the H-NMR spectrum of the dissolved compound (FIG. 8b). If we assume that form IV is an adduct between aspartame and propyleneglycol, the two doublets in the DSC spectrum, the relatively large weight loss apparent from the TG/DTA spectra (a total of 36% wt/wt for the "dehydration" and first decomposition peaks) and the shift towards lower temperatures of the decomposition peak can be readily explained as follows:

According to the NMR spectrum (FIG. 8b) form IV aspartame contains approx. 20% wt/wt of propyleneglycol. It can also be shown that the decomposition of aspartame into diketopiperazine should result in a weight loss of 10.87% wt/wt (corresponding to methanol). Assuming that part of the propyleneglycol emerges in the region of the "dehydration peak" and the rest in the region of the first decomposition peak (i.e. between 150–160° C.) we obtain a reasonable balance of approx. 5% wt/wt corresponding to the content of water in the original compound. The above assumption has been confirmed by heating form IV aspartame at 100° C. for different time intervals (15 min, 30 min and 60 min). H-NMR spectra of the heated products clearly show a gradual decrease of the $CH_3$ peak characteristic of propyleneglycol (1.17–1.19 ppm) with increasing heating time.

H-NMR spectra (FIG. 8) of the compounds dissolved in $D_2O$ were recorded on a Brucker AMX 3000 NMR spectrometer. The spectra give information on the molecular structure of the new crystal forms. The spectrum of form III is identical to that of NUTRASWEET aspartame (FIG. 8a) while the spectrum of form IV (FIG. 8b) exhibits in addition three peaks in regions characteristic for protons of propyleneglycol, i.e. (in ppm) (a) 1.17–1.19 for the $CH_3$ group, (b) 3.45–3.62 for the $CH_2$ group and (c) 3.91–3.92 for the CH group. By relating the integral of peak (a) to the integral of the peak corresponding to the $CH_3$ group of aspartame (3.8 ppm) we could show that the aspartame/propyleneglycol molar ratio in the new compound was approx. 1:1 or 20% wt/wt. If by cleaning additional propylene glycol was removed, the previously described form IIA was obtained. We therefore concluded that form IV is an adduct of aspartame with propyleneglycol.

Figure 9A:
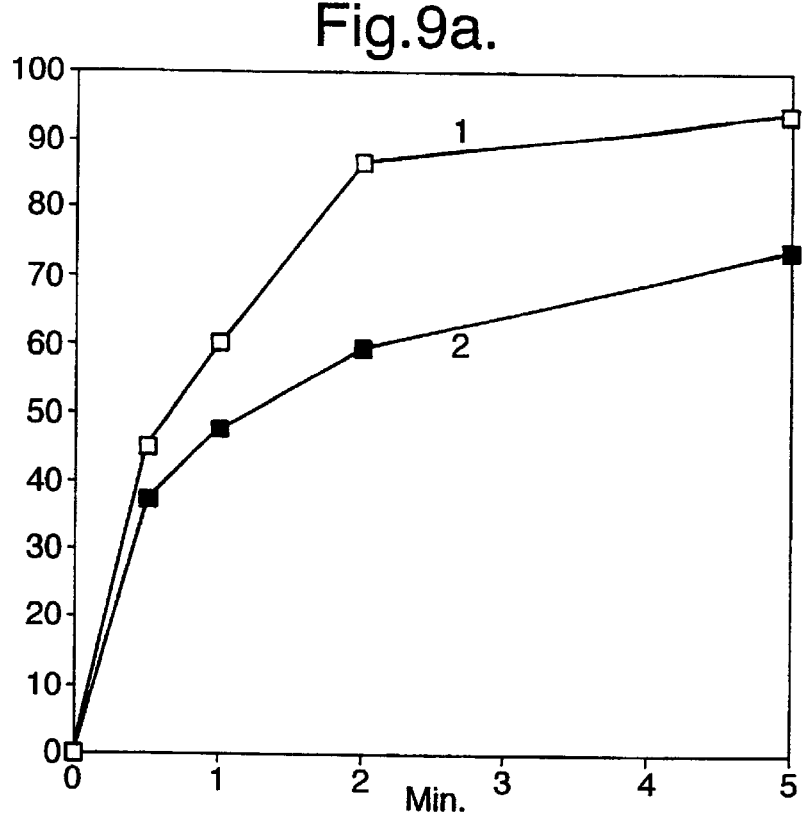
FIG. 9a having conditions of 25° C.

Dissolution kinetics: 1 gr of powdered form III aspartame and NUTRASWEET® aspartame both ground in a ball mill to an average particle size 1.5 μm were each suspended in 100 ml of deionised water and stirred at 750 rpm for 1 hour. During dissolution the samples were kept at constant temperature (45° and 25° C.). Aliquots of 0.5 ml were taken at predetermined time intervals and aspartame in the solution was determined by UV spectrometry. The results obtained during the first 5 minutes of dissolution (FIGS. 9a,b) convincingly show thlat the initial rate of dissolution was considerably higher for form III as compared to commercial NUTRASWEET® aspartame. In addition we note that >97% of form III aspartame was dissolved within 5 min at 45° C., and within 30 min at 25° C., while with NUTRASWEET® aspartame the same was achieved within 10 min at 45° C. and within 60 min at 25° C.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A method of preparing new crystal forms of aspartame utilizing microemulsions comprising:

(a) introducing aspartame into a microemulsion formed from an oil phase, an aqueous phase and at least one emulsifier;

(b) destabilizing said microemulsion to effect recrystallization of aspartame;

(c) separating solid phase crystals from the liquid phase in which they are contained; and (d) cleaning said crystals to remove traces of the oil phase and surfactant.

2. A method according to claim 1, wherein crystals are cleaned with a suitable solvent and said method further comprises:

(e) removing the solvent by drying said crystals.

3. A method according to claim 1, wherein aspartame is solubilized in a hot microemulsion and said microemulsion is destabilized by cooling.

4. A method according to claim 1, wherein said microemulsion is a water-in-oil microemulsion stabilized by a double-chained anionic emulsifier.

5. A method according to claim 4, wherein said oil is selected from the group consisting of hydrocarbons and liquid triglycerides.

6. A method according to claim 4, wherein said double-chained anionic emulsifier is sodium diisooctyl sulfosuccinate (AOT).

7. A method according to claim 1, wherein said microemulsion is a water-in-oil microemulsion stabilized by a non-ionic food-grade emulsifier.

8. A method according to claim 7, wherein said non-ionic food-grade emulsifier comprises 10% wt/wt L-α-phosphatydilcholine and 90% wt/wt of monoglycerooleate dissolved in propyleneglycol.

9. A method according to claim 7, wherein said oil is selected from the group consisting of hydrocarbons, liquid triglycerides, alcohols, acids, ketones, esters, aldehydes, terpenes, essential oils and oleoresins.

10. A method according to claim 9, wherein said oil is isooctane.

11. A method according to claim 9, wherein said oil is soybean.

12. A method according to claim 1, wherein aspartame is crystallized from said microemulsion at low temperature without forced convection.

13. A method according to claim 1, wherein the product is cleaned with a water immiscible solvent.

14. A method according to claim 13, wherein said water immiscible solvent is hexane.

15. A method according to claim 1, wherein the solid phase is separated from the liquid phase by filtration.

16. A method according to claim 1, wherein the solid phase is separated from the liquid phase by centrifugation.

17. A method according to claim 1, wherein said microemulsion is a water-in-oil microemulsion.

18. A method according to claim 17, wherein said microemulsion is stabilized by a zwitterionic emulsifier.

19. A method according to claim 17, wherein said microemulsion is stabilized by a cationic food-grade emulsifier.

Figure 3B:
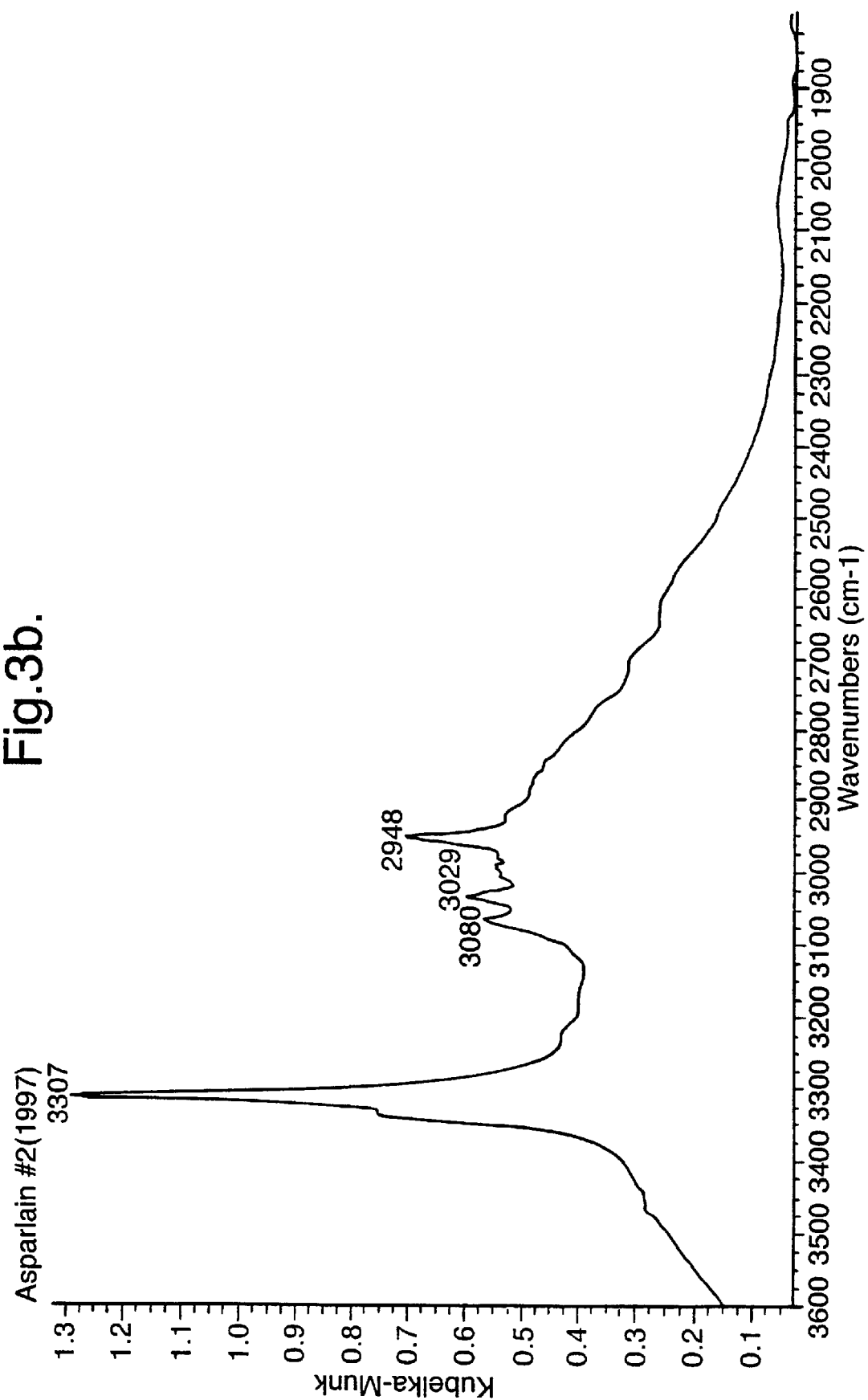
FIG. 3 shows Fourier Transform Infrared (FTIR) spectra taken between 3600–1900 $cm^{-1}$ (a) NUTRASWEET® aspartame, (b) form III, (c) form IV.
Figure 4A:
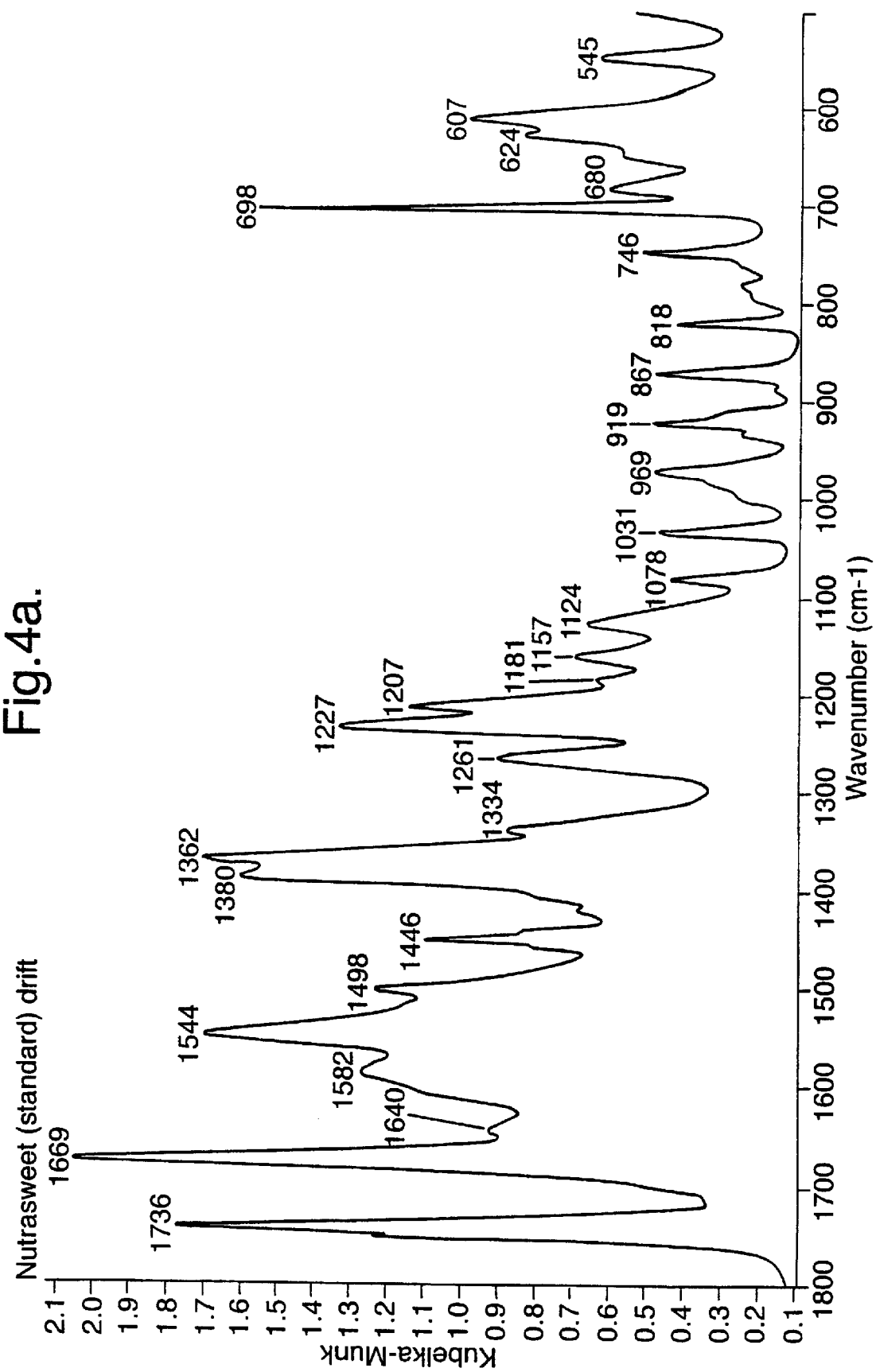
FIG. 4 shows FTIR spectra taken between 1800–650 cm$^{-1}$:
(a) NUTRASWEET® aspartame
(b) form III (1800–700 cm-1), and
(c) form IV.
Figure 4B:
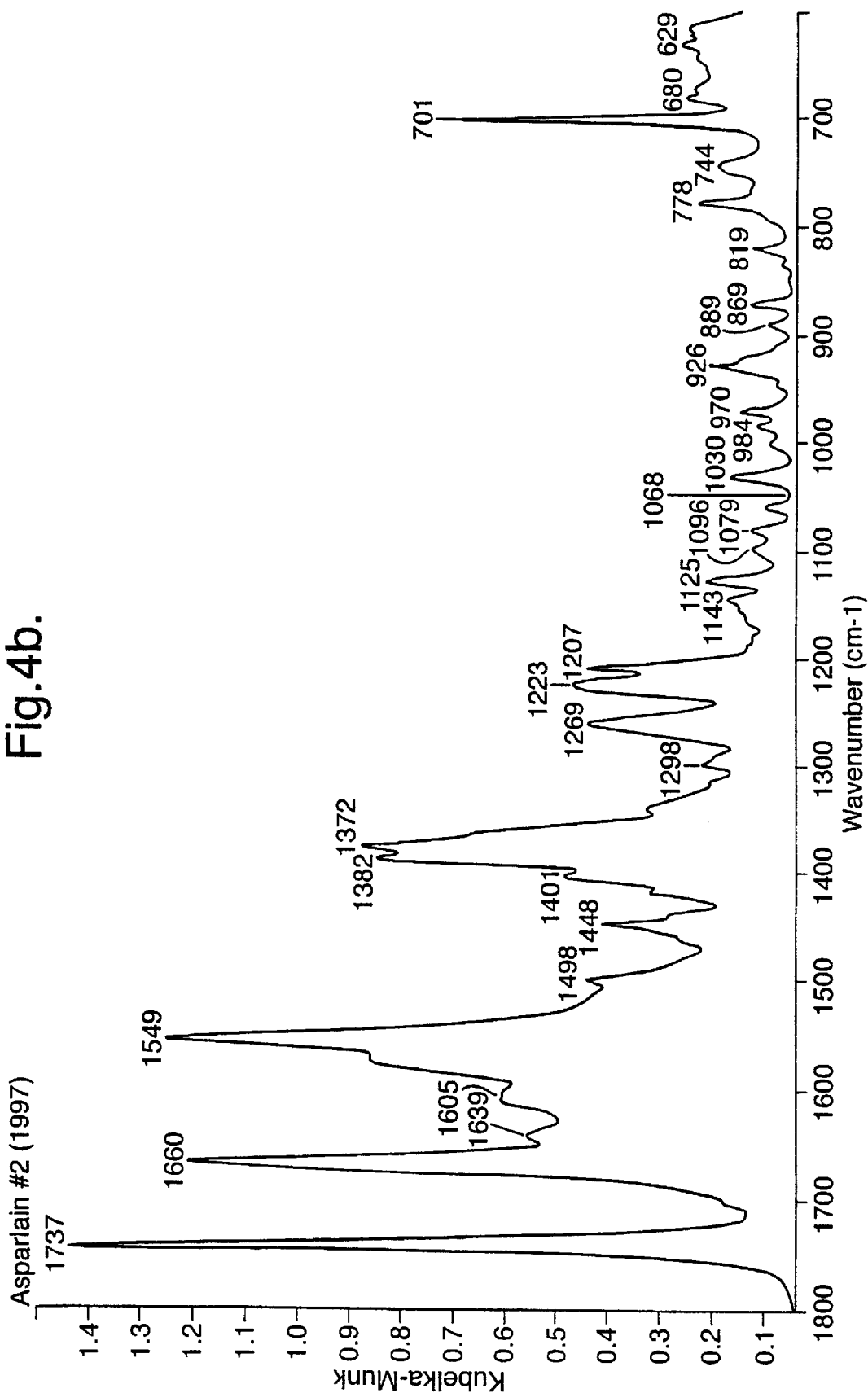
Figure 5B:
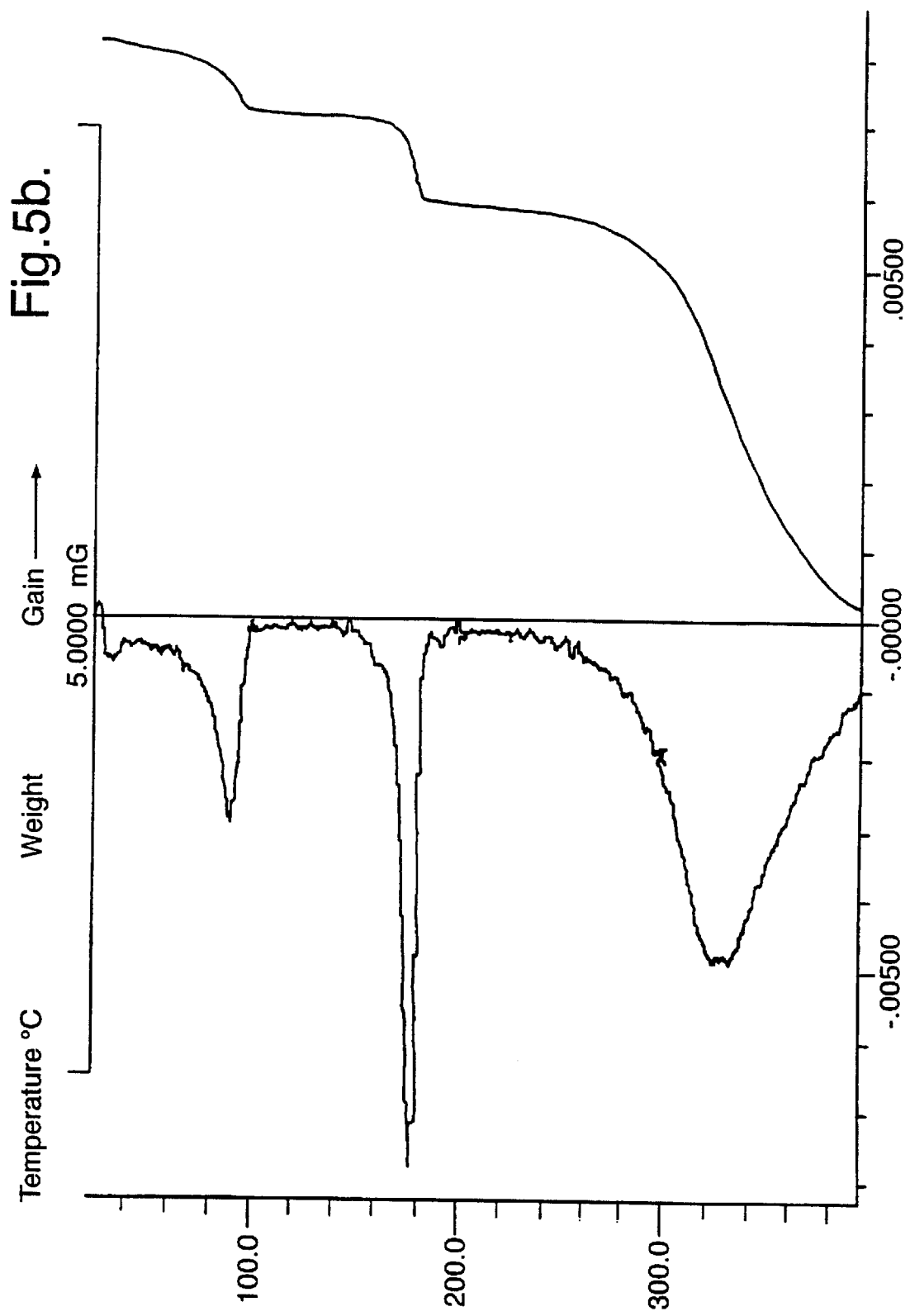
Figure 9B:
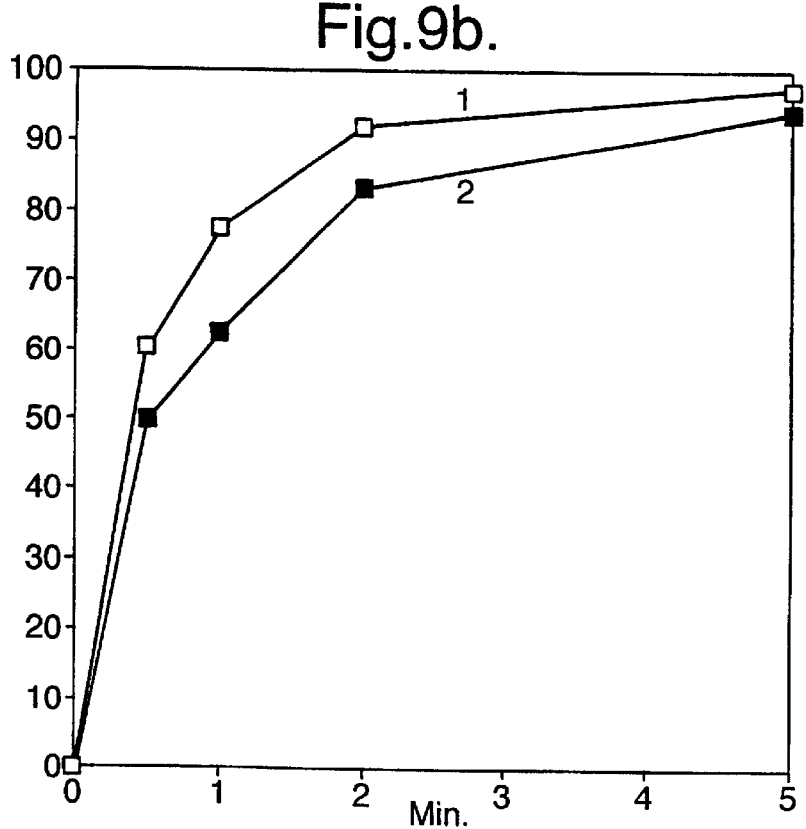
FIG. 9b having conditions of 45° C. Curves 1—form III aspartame, Curves 2—NUTRASWEET® aspartame. Both samples were ground to an average particle size of 1.5 μm.

20. A crystal form of aspartame designated APM III obtained according to claim 1 characterized by:
   (a) an X-ray diffraction powder pattern (angles of diffraction) as set forth in FIG. 1b herein;
   (b) an FTIR spectrum as represented in FIGS. 3b and 4b herein;
   (c) TG/DTA and DSC patterns as represented in FIG. 5 appended hereto; and
   (d) improved dissolution kinetics as compared to commercial NUTRASWEET® aspartame as shown in FIG. 9 herein.

Figure 3C:
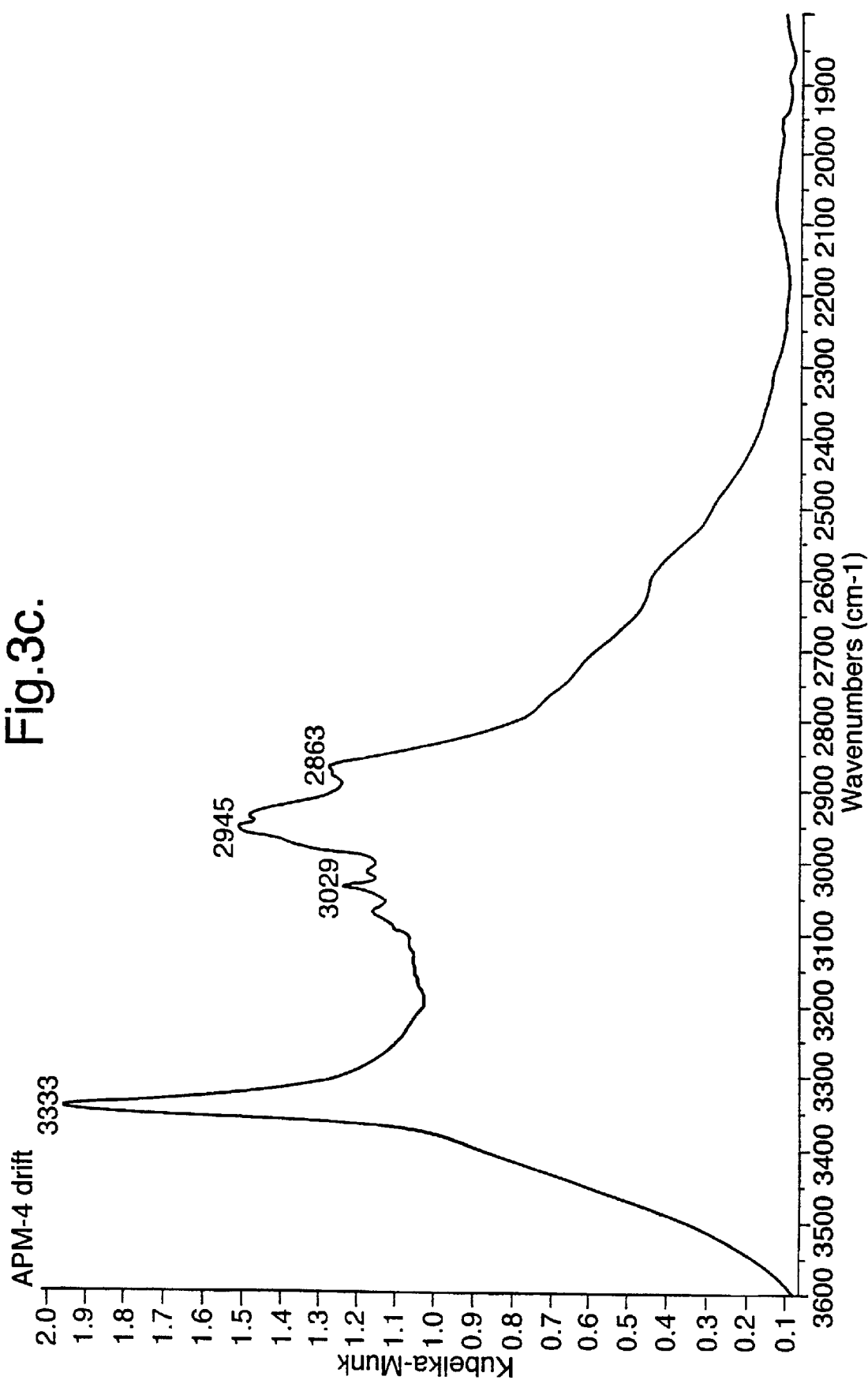
Figure 4C:
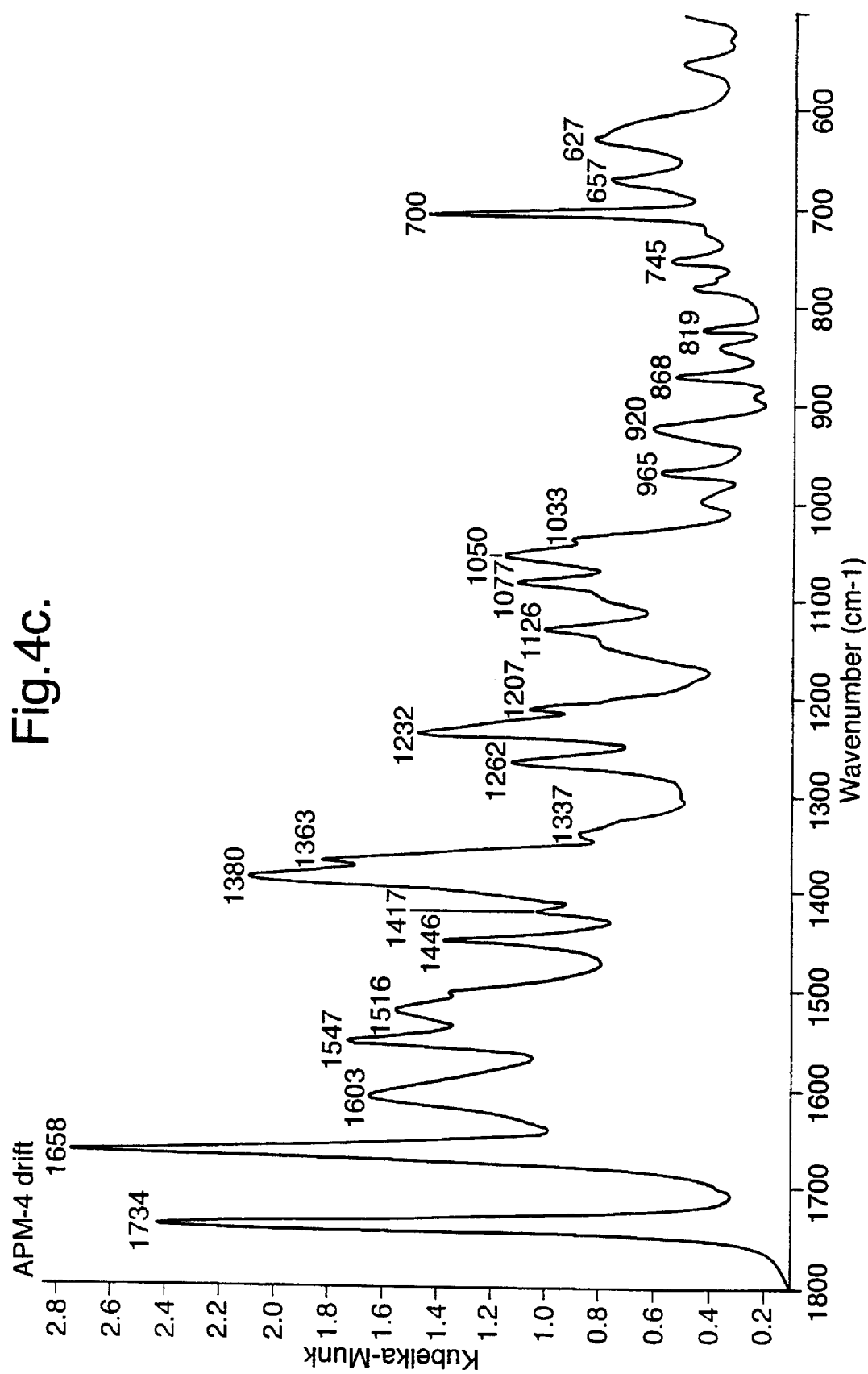
Figure 6A:
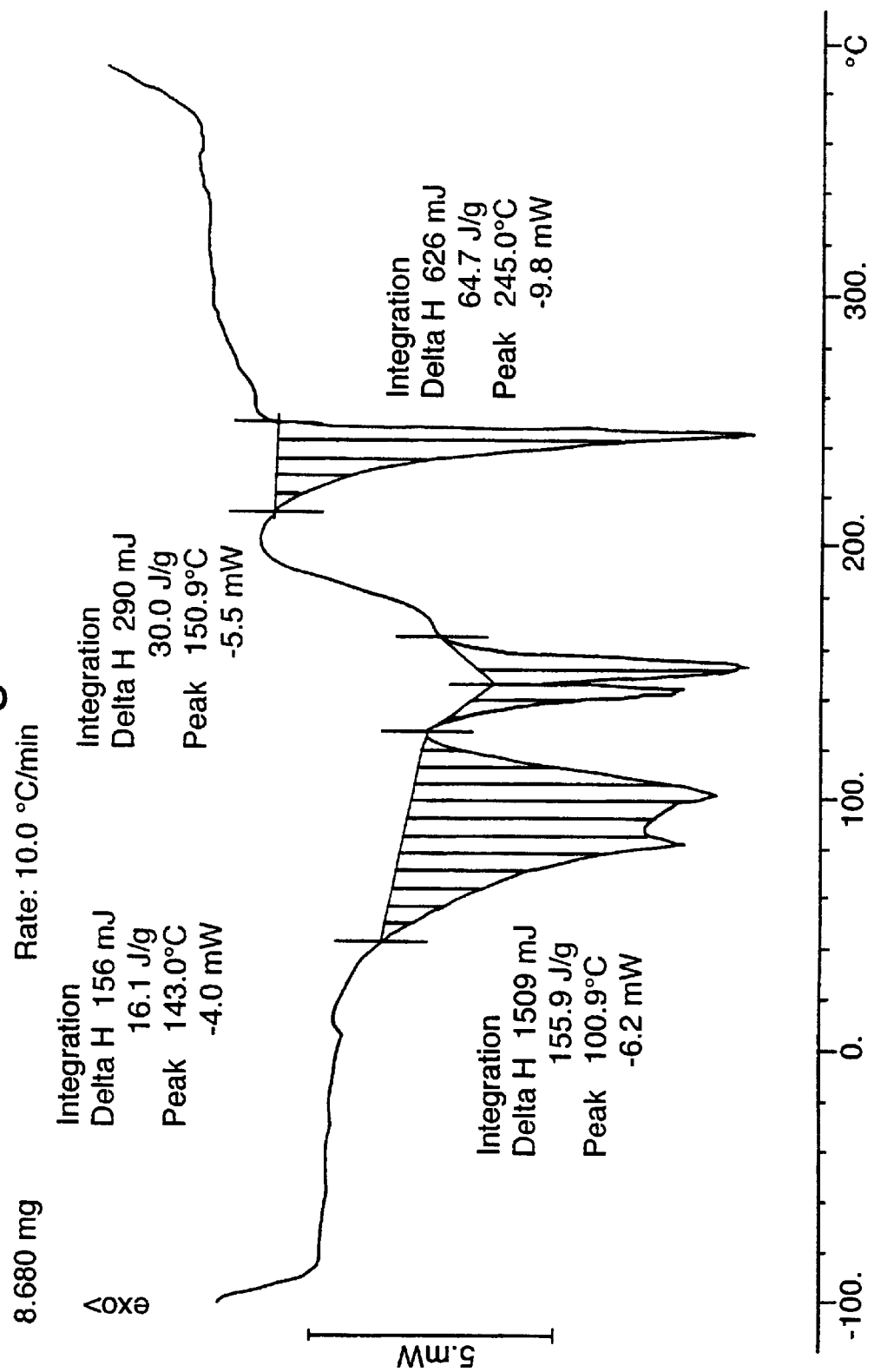
FIG. 6a DSC and FIG. 6b illustrates TG and DTA spectra.
Figure 6B:
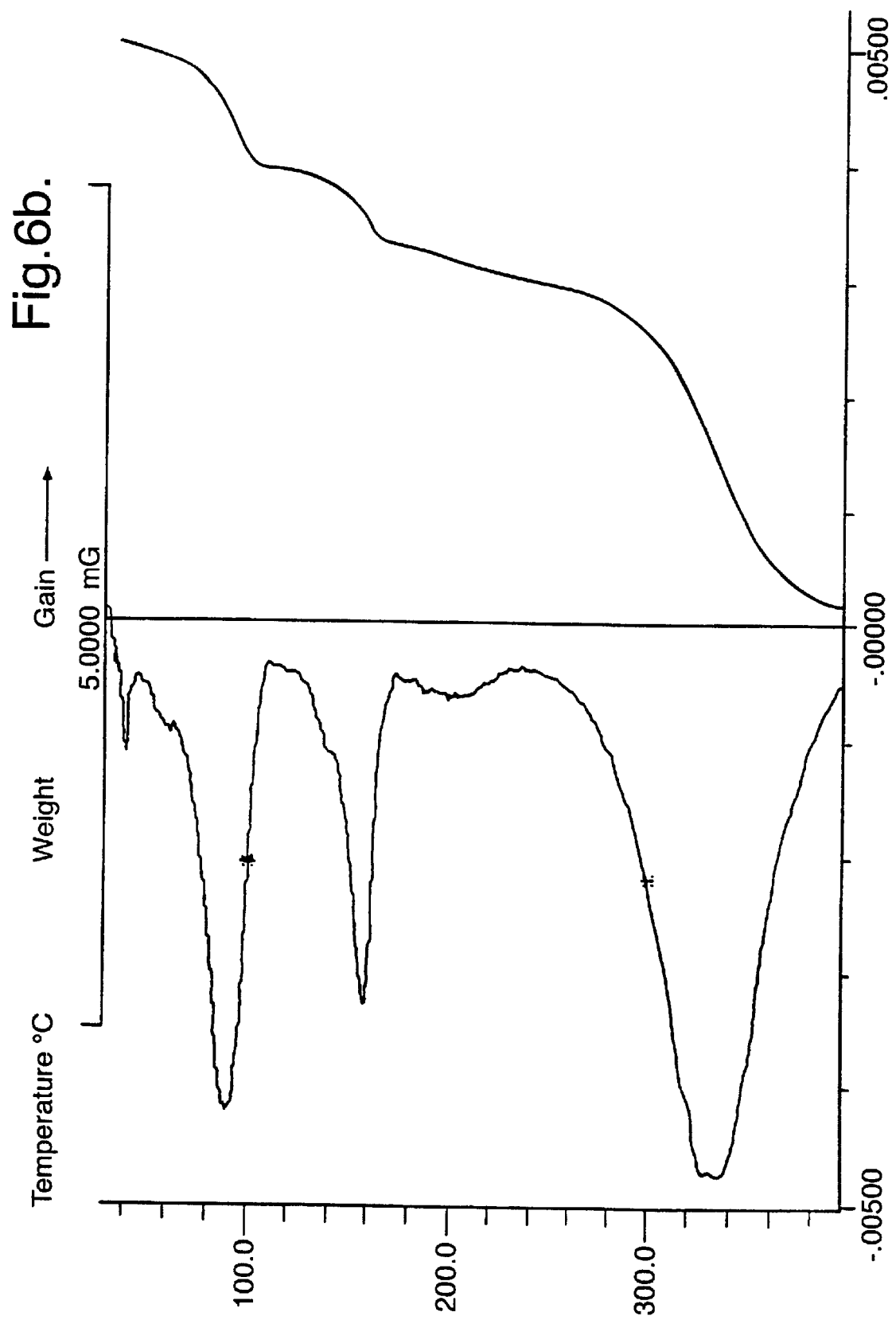
Figure 7B:
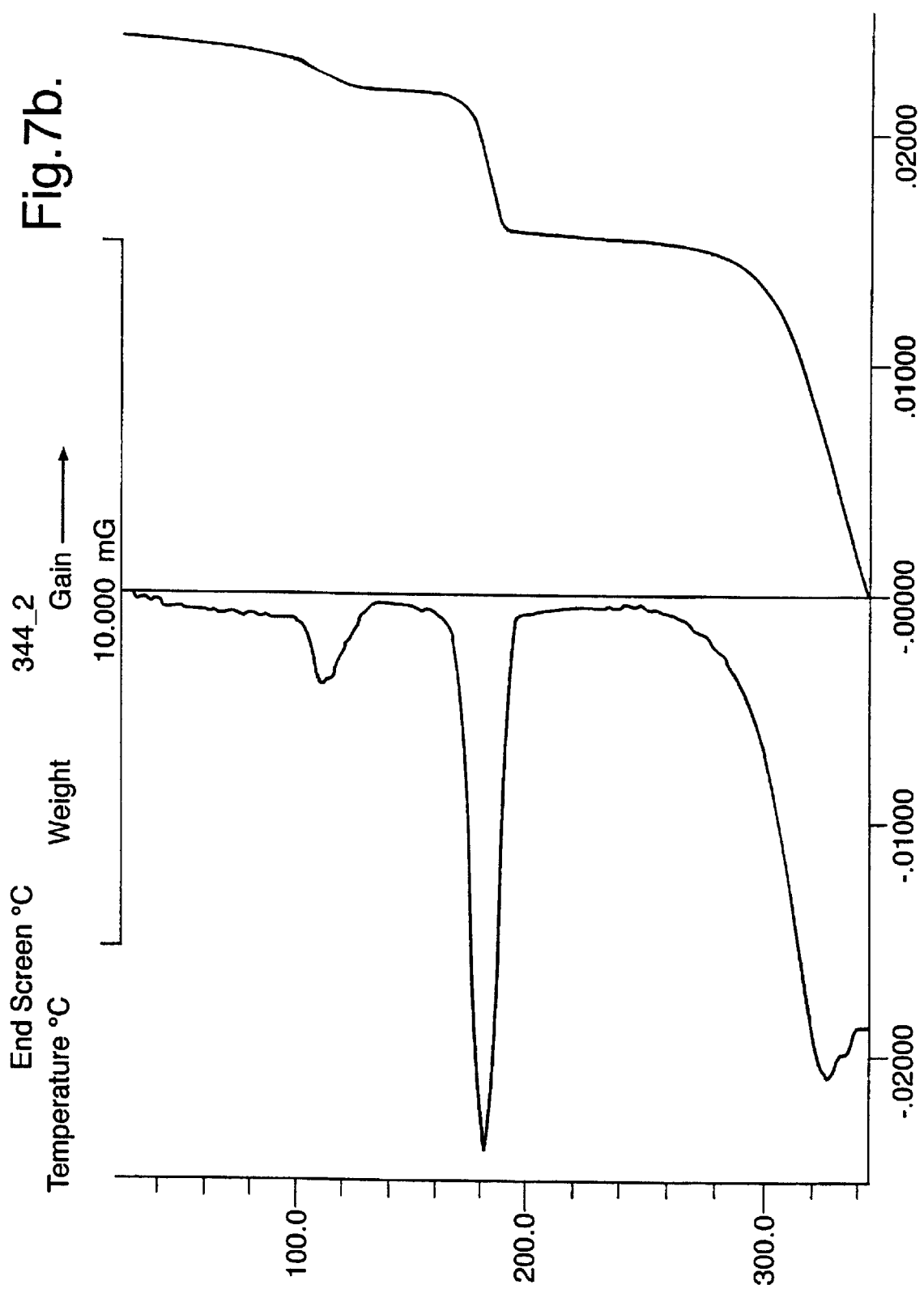

21. A crystal form of aspartame designated APM IV obtained according to claim 1 characterized by:
   (a) an X-ray diffraction powder pattern (angles of diffraction) as set forth in FIG. 1c herein;
   (b) an FTIR spectrum as represented in FIGS. 3c and 4c herein;
   (c) TG/DTA and DSC patterns as represented in FIG. 6 appended hereto; and
   (d) an H-NMR spectrum of crystals dissolved in $D_2O$ as represented in FIG. 8b herein.

* * * * *